US008696727B2

(12) United States Patent
Emon

(10) Patent No.: US 8,696,727 B2
(45) Date of Patent: Apr. 15, 2014

(54) COOLING DEVICES

(75) Inventor: Lynda Emon, Spring Park, MN (US)

(73) Assignee: Lynda Emon, Minneapolis, MN (US)

( * ) Notice: Subject to any disclaimer, the term of this patent is extended or adjusted under 35 U.S.C. 154(b) by 15 days.

(21) Appl. No.: 13/612,372

(22) Filed: Sep. 12, 2012

(65) Prior Publication Data

US 2013/0006338 A1  Jan. 3, 2013

Related U.S. Application Data

(62) Division of application No. 11/897,783, filed on Aug. 31, 2007, now abandoned.

(60) Provisional application No. 60/842,101, filed on Sep. 5, 2006, provisional application No. 60/958,676, filed on Jul. 9, 2007.

(51) Int. Cl.
*A61F 7/00* (2006.01)

(52) U.S. Cl.
USPC .......................................................... 607/114

(58) Field of Classification Search
USPC .......................................................... 607/114
See application file for complete search history.

(56) References Cited

U.S. PATENT DOCUMENTS

| | | | |
|---|---|---|---|
| 1,576,488 A | 3/1926 | Hodgson | |
| 2,563,933 A | 8/1951 | Hipps et al. | |
| 4,577,625 A * | 3/1986 | Lohati et al. | ................... 601/128 |
| 4,688,572 A | 8/1987 | Hubbard et al. | |
| 4,783,866 A | 11/1988 | Simmons et al. | |
| 4,805,619 A | 2/1989 | Swearingen | |
| 4,858,259 A | 8/1989 | Simmons et al. | |
| 4,910,978 A | 3/1990 | Gordon et al. | |
| 5,031,418 A | 7/1991 | Hirayama et al. | |
| 5,088,487 A | 2/1992 | Turner et al. | |
| 5,088,549 A | 2/1992 | Schneider | |
| 5,257,429 A | 11/1993 | Genis | |
| 5,274,865 A | 1/1994 | Takehashi | |
| 5,295,949 A | 3/1994 | Hathaway | |
| 5,375,278 A | 12/1994 | Vanwinkle et al. | |
| 5,400,617 A | 3/1995 | Ragonesi | |
| 5,507,793 A | 4/1996 | Hodges | |
| 5,584,086 A | 12/1996 | VanWinkle et al. | |
| 5,716,388 A | 2/1998 | Petelle | |
| 5,971,947 A | 10/1999 | Mcnally et al. | |
| 6,017,606 A | 1/2000 | Sage et al. | |
| 6,024,762 A * | 2/2000 | Gray | .............................. 607/109 |
| 6,083,254 A | 7/2000 | Evans | |
| 6,149,617 A | 11/2000 | Mcnally et al. | |
| 6,190,288 B1 | 2/2001 | Fisher | |
| 6,554,787 B1 | 4/2003 | Griffin et al. | |

(Continued)

OTHER PUBLICATIONS

U.S. Appl. No. 11/897,783, Examiner Interview Summary mailed Aug. 16, 2012, 3 pgs.
U.S. Appl. No. 11/897,783, Final Office Action mailed Apr. 12, 2012, 9 pgs.

(Continued)

*Primary Examiner* — Linda Dvorak
*Assistant Examiner* — Kaitlyn Smith
(74) *Attorney, Agent, or Firm* — Schwegman, Lundberg, & Woessner, P.A.

(57) ABSTRACT

This invention is directed to the application of portable and reusable cooling devices that comprise fabric covered pillowettes filled with either an herbal blend or a self-contained gel pack designed to be frozen before application directly to the skin of hot or bruised humans and animals to relieve heat distress or swelling.

4 Claims, 5 Drawing Sheets

(56) References Cited

U.S. PATENT DOCUMENTS

| | | | |
|---|---|---|---|
| 8,197,526 B2* | 6/2012 | Kumamoto et al. | 607/114 |
| 2004/0073281 A1* | 4/2004 | Caselnova | 607/111 |
| 2004/0250778 A1 | 12/2004 | Bennis | |
| 2005/0261755 A1 | 11/2005 | Bacino et al. | |
| 2006/0276863 A1* | 12/2006 | Kumamoto et al. | 607/96 |
| 2007/0225782 A1 | 9/2007 | Taylor | |
| 2008/0119916 A1 | 5/2008 | Choucair et al. | |
| 2008/0195065 A1 | 8/2008 | Renzin et al. | |
| 2008/0289351 A1 | 11/2008 | Taylor | |
| 2009/0030491 A1 | 1/2009 | Justice-black | |
| 2009/0157153 A1* | 6/2009 | Lemke et al. | 607/114 |
| 2010/0217363 A1 | 8/2010 | Whitely | |
| 2011/0022138 A1 | 1/2011 | Warner et al. | |
| 2011/0029051 A1 | 2/2011 | Ross | |
| 2012/0191023 A1* | 7/2012 | Young | 601/18 |
| 2013/0085556 A1* | 4/2013 | Gillespie et al. | 607/114 |

OTHER PUBLICATIONS

U.S. Appl. No. 11/897,783, Non Final Office Action mailed Jul. 27, 2011, 5 pgs.

U.S. Appl. No. 11/897,783, Notice of Non-Compliant Response mailed Dec. 7, 2011, 2 pgs.

U.S. Appl. No. 11/897,783, Response filed Jan. 3, 2012 to Non Final Office Action mailed Jul. 27, 2011, 13 pgs.

U.S. Appl. No. 11/897,783, Response filed Jul. 6, 2011 to Restriction Requirement mailed Mar. 6, 2011, 2 pgs.

U.S. Appl. No. 11/897,783, Response filed Nov. 28, 2011 to Non Final Office Action mailed Jul. 27, 2011, 9 pgs.

U.S. Appl. No. 11/897,783, Response filed Nov. 29, 2011 to Non Final Office Action mailed Jul. 27, 2011, 9 pgs.

U.S. Appl. No. 11/897,783, Response filed Dec. 29, 2011 to Non Final Office Action mailed Jul. 27, 2011, 13 pgs.

U.S. Appl. No. 11/897,783, Restriction Requirement mailed Jun. 6, 2011, 5 pgs.

* cited by examiner

*Fig. 4*
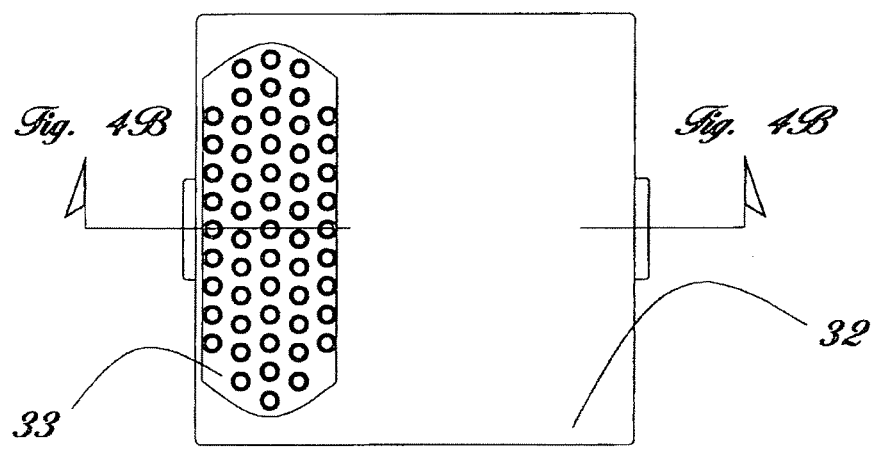
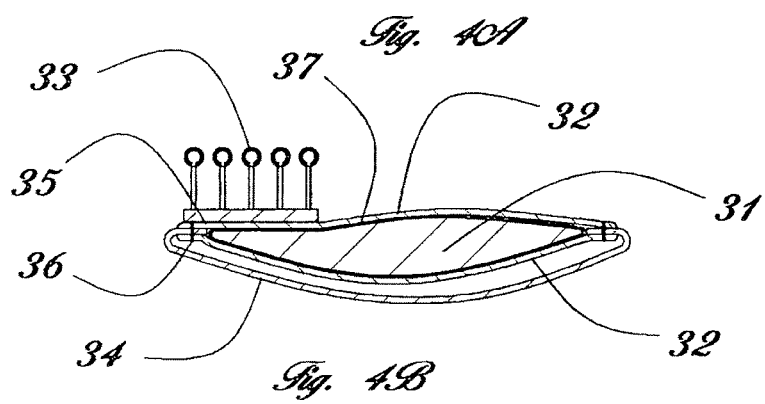
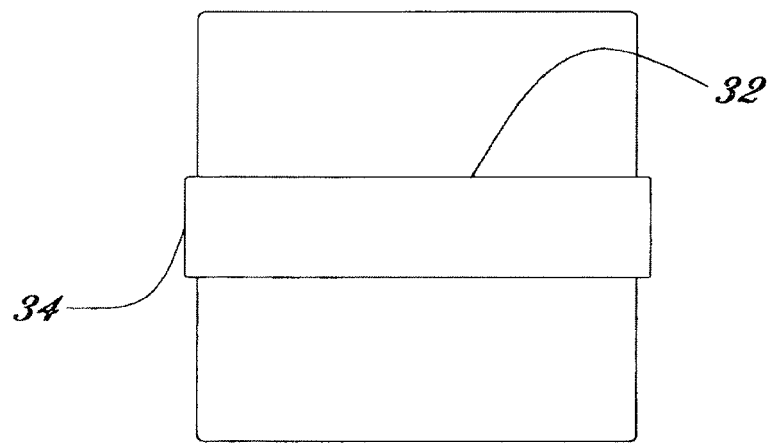

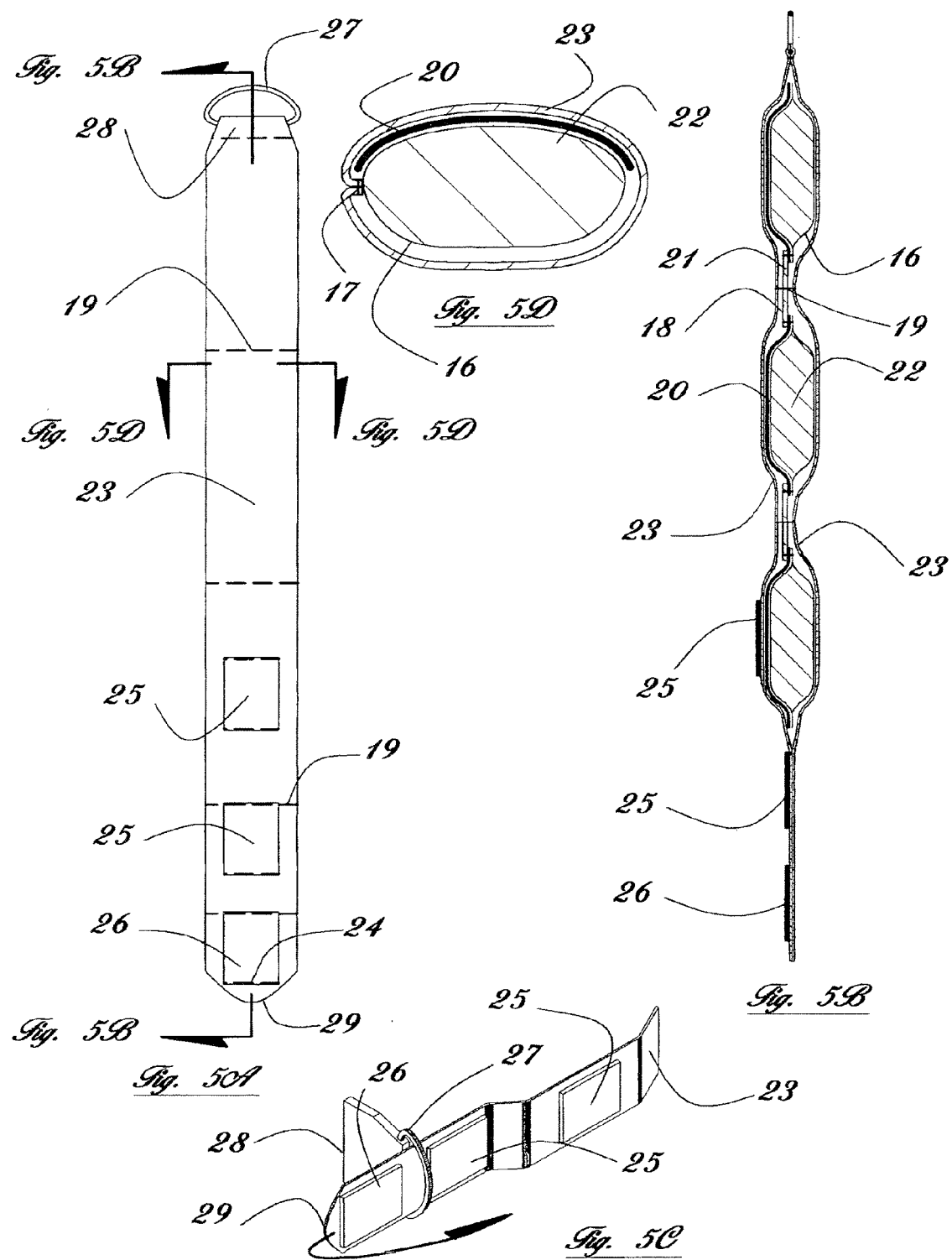

COOLING DEVICES

CLAIM OF PRIORITY

This application is a divisional of and claims the benefit of priority under 35 U.S.C. §120 to U.S. patent application Ser. No. 11/897,783, filed on Aug. 31, 2007, which claims the benefit of priority under 35 U.S.C. §119(e) to U.S. Provisional Patent Application Ser. No. 60/842,101, filed on Sep. 5, 2006, and to U.S. Provisional Patent Application Ser. No. 60/958,676, filed on Jul. 9, 2007, the benefit of priority of each of which is claimed hereby, and each of which are incorporated by reference herein in its entirety.

FIELD OF THE INVENTION

This invention relates generally to body coolers, specifically to devices designed to be frozen.

BACKGROUND OF THE INVENTION

A personal coolant device used down the front of bra pressed against the sternum brings about heat and anxiety relief as well as a feeling of well-being. The aromatic satin pillowettes seen in FIG. 2 and FIG. 3 are filled with a blend of aromatics and flax seeds which is a perfect conductor of cryogenics. Said invention is a delightful and important personal accessory for females dealing with heat related distress whether from hot flashes, exercise, excessive perspiration related to menopause or body heat surges from post surgery medication withdrawal or any nervous situation. The cold pillowette anchors under the fabric partition between the cups of a bra.

Gel coolant pillowettes as seen in FIG. 1 maintain a longer lasting chill for over an hour once placed down the front of a bra where it is pressed against the sternum or placed on the back of the neck. The cotton fabric covering insulates the gel pack and keeps it from burning the skin. The loop at the top is useful for hanging the device from a necklace to reach other parts of the body. It is also a handy place from where to hang eye glasses, once in position in cleavage. It is an excellent product for all menopausal symptoms like hot flashes and night sweats, panic attacks, facial swelling from Botox injections and stressful situations like public speaking. It is very useful when applied directly to personal regions when experiencing soreness from sex, surgical soreness from labiaplasty, hemorrhoids, milk engorged breasts, prostate cancer surgery soreness and the like.

People who prefer to blot and dab perspiration or reduce surgical swelling and bruising use the hand-held gel pad with the strap as seen in FIG. 4. The fabric covering is generally cotton or a soft absorbent material. The brush attachment on the under side of the device turns it into a grooming device for hot animals. The glamorous marabou feathers glued across the length of the strap makes it an appealing feminine device to hold in the hand and dab on themselves or their pets to relieve local heat and bruising.

When further industrial strength body cooling is required, a gel neck wrap (as seen in FIG. 5.) as worn either alone or in combination with a gel pack in cleavage, is indispensable. It is especially useful when out of doors while working up a sweat when hiking and biking, athletics such as golf and tennis, motorcycle riding, working construction, gardening, cooking, cleaning, BBQ-ing, postal working or for military detail. The insulator feature between the gel pack and the outer layer of fabric reflects sunlight so it stays cold nearly twice as long as without the insulator.

The gel material is made of a polymer and water and is prepackaged in a plastic wrapper so it is not wet. Because it is not wet and the gel crystals are not deposited loosely into the fabric sections, it does not get moldy and sour. The gel packs easily refreeze over and over and never wear out. The freeze point is −2C and the freezer set-up temperature is −9C. They take 30 minutes to freeze and gently thaw in about 2 hours.

Dogs get most of their cooling from evaporation of moisture from the lungs, nose and mouth. They pant when they are hot to capture moisture and get it into the circulatory system. The gel neck wrap temporarily cuts down on hyperventilation needed to cool down a hot dog.

SUMMARY OF INVENTION

The present invention is directed to a cooling pillowette comprising: a closed oblong fabric casing having a top end and a bottom end; a gel pack comprising an oblong sealed plastic wrapper encasement filled with gel material, the gel pack enclosed within the oblong fabric casing; and a loop secured to the top end of the oblong fabric casing and extending out from the top end.

Another embodiment of the invention is directed to a cooling pillowette comprising: an enclosed fabric casing having a generally heart-shape with a convex front and convex rear walls joined by a continuous perimeter wall, the fabric casing having an interior chamber, the heart-shape fabric casing having a seam in its continuous perimeter wall for filling the interior of the casing; a gel bubble comprising a sealed plastic wrapper encasement filled with gel material, the gel bubble positioned generally in the central area of the interior chamber of the enclosed fabric casing; and a stuffing of an herbal blend within the interior chamber to shape the fabric casing so that the front and rear walls of the casing are convex and to support the gel bubble generally in the central area of the interior chamber of the fabric casing.

Another embodiment of the present invention comprises a hand-held body cooling device comprising: a closed fabric encasement prepared from a single piece of fabric and having opposing spaced apart front and back walls joined at their periphery, opposing first and second side seams forming a portion of the periphery; a strap comprising a flat webbing having first and second opposing sides and crossing the midportion of the back wall, the first end of the flat webbing secured in the first side seam and the second end of the flat webbing secured in the second side seam; and a gel pack comprising a sealed plastic wrapper encasement having generally the shape of the enclosed fabric encasement, the plastic wrapper encasement filled with gel material, the gel pack enclosed within the closed fabric encasement.

The cooling pillowette can have a generally square shape, a rectangular shape, an oval shape, or a round circle shape.

The cooling pillowette can include a brush element comprising a generally planar backbone with a plurality of brush tines extending upward perpendicularly from the backbone, the backbone secured to the front side of the fabric casing. The brush can be positioned parallel with respect to the strap. The brush can be positioned on a portion of the periphery of the enclosed fabric encasement pocket, or it can be secured in a mid-portion of the front wall of the enclosed fabric encasement pocket.

The hand-held body cooling device can include a strip of decorative feathers secured to the surface of the flat webbing of the strap facing outward from the cooling device.

Another embodiment of the present invention is directed to an insulated gel neck wrap comprising a fabric casing having an inner wall and an opposing outer wall and opposing first and second end portions; a chain comprising a plurality of spaced apart gel packs, the gel packs having opposing inner and outer walls and first and second opposing ends, adjacent gel packs joined by a flexible link, the link secured to an end of each adjacent gel pack, the chain positioned in the fabric casing between the first and second end portions, each link secured to the inner and outer wall of the fabric casing; and a means to detachably join the first and second end portions of the casing.

Preferably the inner wall of each gel pack faces the interior side of the inner wall of the fabric casing and the outer wall of each gel pack faces the interior side of the outer wall of the fabric casing.

In the preferred embodiment, the insulated gel neck wrap includes a plurality of insulators, each insulator associated with a gel pack and covering the outer wall of the associated gel pack with each insulator positioned between the interior side of the outer wall of the fabric casing and the outer wall of the associated gel pack.

Preferably each link is an elastic fabric. Most preferably the ends of each link are secured to the ends of the adjacent gel packs and to the ends of the insulators associated with the gel packs.

The means to detachably join the first and second end portions of the fabric casing can comprise a ring secured to the first end portion of the fabric casing, the second end portion of the fabric casing adapted to be received through the ring and doubled over toward the inner wall of the fabric casing so that the second end portion is detachably joined to the ring; a hook pad secured to the inner wall of the fabric casing proximate the end of the second end portion of the fabric casing, a plurality of loop pads secured to the inner wall of the fabric casing between the loop pad and the first end portion of the fabric casing, the hook pad adapted to be detachably secured to a loop pad when the second end portion of the fabric casing is doubled over toward the inner wall of the fabric casing to detachably join the first end portion to the second end portion of the fabric casing.

BRIEF DESCRIPTION OF THE DRAWING

FIG. 1A is the front perspective view of the present invention;

FIG. 1B is the left side perspective of present invention;

FIG. 2A is the front perspective of the present invention;

FIG. 2B is the side perspective view of the present invention.

FIG. 3A is the front perspective view of the present invention;

FIG. 3B is the perspective side view of said invention;

FIG. 4 is the plan view of present invention;

FIG. 4A is the plan under side of present invention;

FIG. 4B is the longitudinal cross section of the present invention;

FIG. 4C is the plan top side of the present invention;

FIG. 5 is the plan view, lateral cross section, exploded view of the adjustment process and the longitudinal cross section of the present invention;

FIG. 5A is the plan view of said invention;

FIG. 5B is the lateral cross section of said invention;

FIG. 5C is the exploded view of the adjustment process;

FIG. 5D is the longitudinal cross section of the present invention;

DETAILED DESCRIPTION OF THE INVENTION

Figure 1:
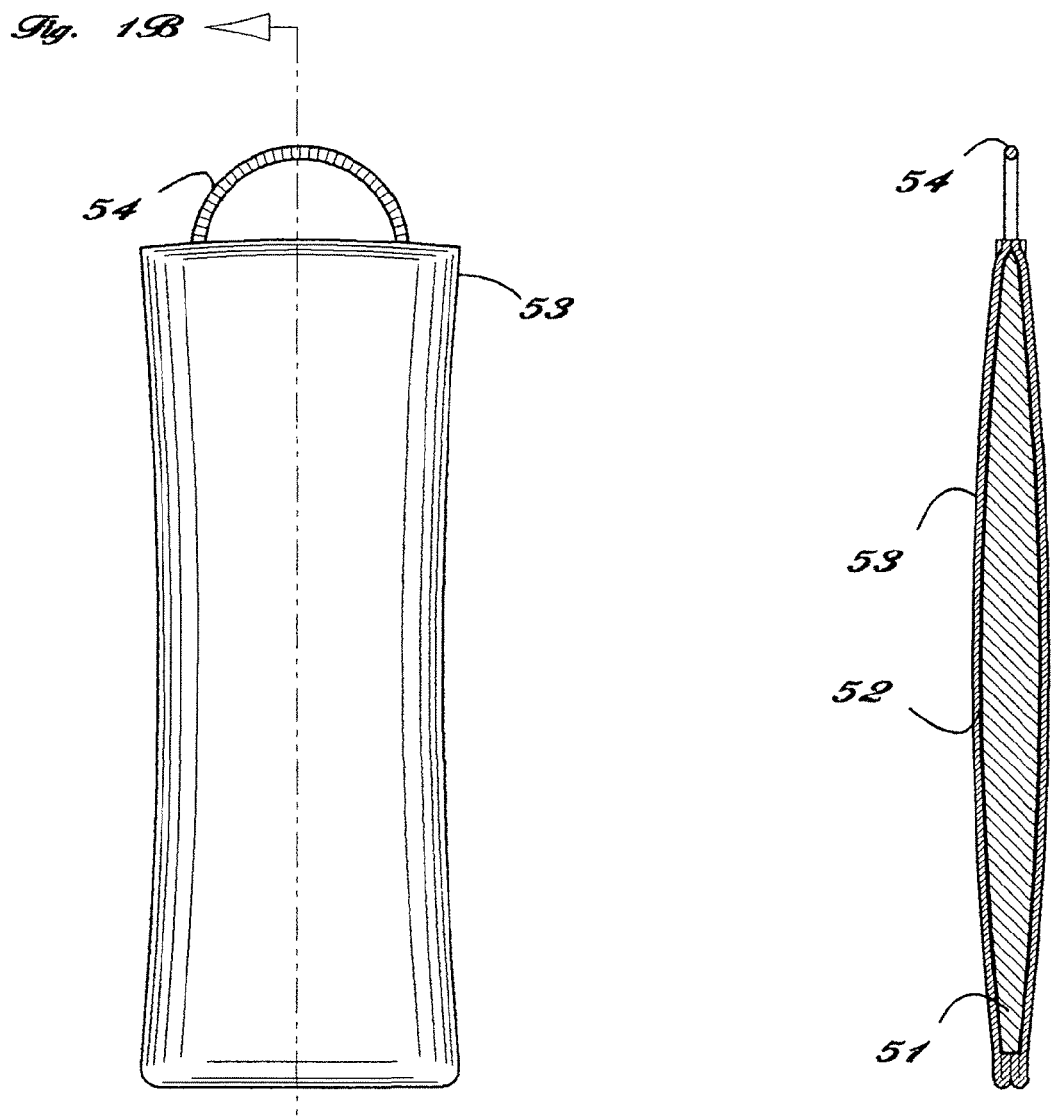
FIG. 1 is the plan view of the present invention

FIG. 1 of the present invention is directed to a body cooler that is a fabric covered gel pillowette. Said gel material is made of polymer and water and is contained in a plastic wrapper. The outer fabric encasement is cut flat with the lengthwise grain. It is folded lengthwise with right sides together and stitched down one side and across the bottom.

Once trimmed close to stitching it is turned right side out and pressed. The gel pack slides in through the top opening. The top opening lips are folded down into the casing with a length of cord inserted at both ends to create a loop extending outwards and layers are top stitched together close to the edge.

Figure 2:
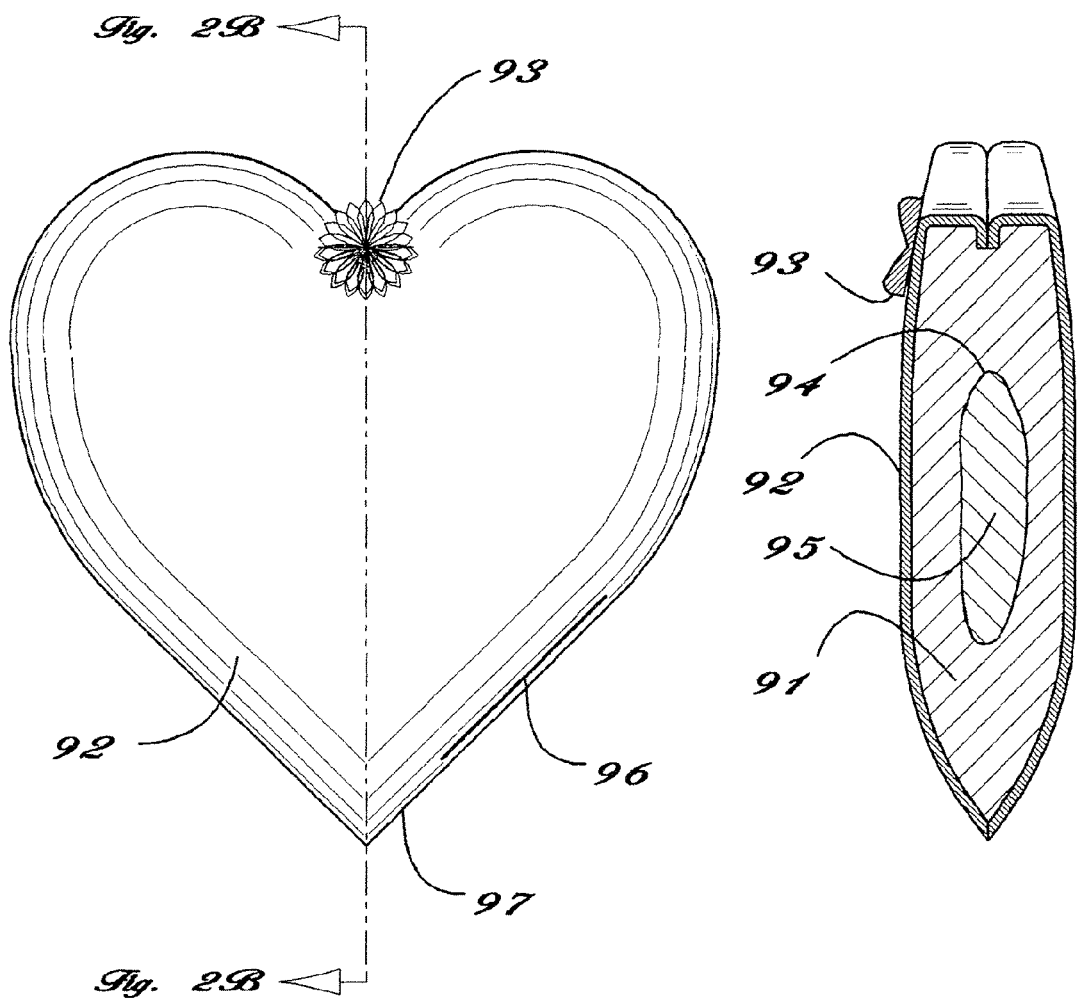
FIG. 2 is the plan view of the present invention.

FIG. 1A is the front plan view of the present invention;
(53) is the one side seam line of the outer fabric casing
(54) is the cord loop sewn into the top seam
FIG. 1B is the left side perspective of the present invention;
(51) is the gel material
(52) is the plastic wrapper containing the gel
(53) is the outer fabric casing
(54) is the position of the cord loop FIG. 2 is the heart shaped aromatherapy body cooler. The fabric is cut flat from a pattern and folded on one side during construction. It is stitched with right sides together around the circumference with 2 lines of parallel stitching close together for safety leaving a 2 inch opening on the lower side for turning and filling and to be top stitched for closure. It is then stitched about 1" more to the bottom point. While inside out it is trimmed close to the stitching line while paying close attention to the cleavage of the heart and also clipping the seam allowance at the bottom most point of the heart on the diagonal. It is turned right side out and tight corners are pushed out with a pointy blunt object. It is then lightly pressed, paying close attention to the crispness of the point and the lips of the opening margin. The gel bubble is inserted first and the herbal filling is funneled in and around it. The opening is then tightly pinned at the closure and top stitched close to the edge with matching thread. A small rosette is glued into the cleavage of the heart for finishing. Once frozen and placed down the front of a bra it delivers astounding and comforting relief from heat and anxiety.

Figure 3:
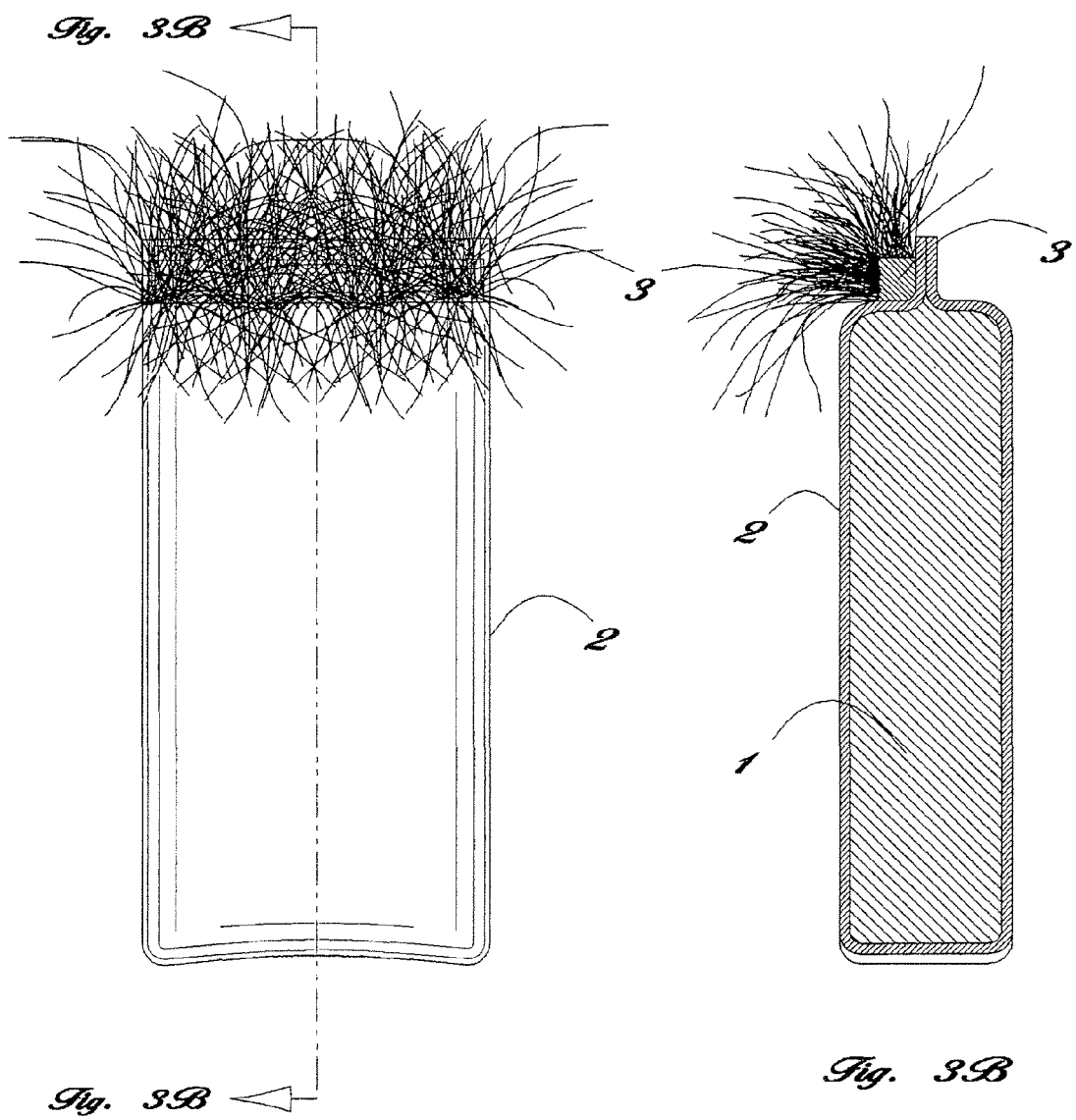
FIG. 3 is the plan view of the present invention.

FIG. 2A is the front perspective view of the present invention;
(92) is the outer fabric
(93) is the embellishment
(96) is the space left open for turning and filling
(97) is the area to create the bottom most end point of the heart
FIG. 2B is the cross section of the present invention;
(91) is the herbal filling
(92) is the outer fabric casing
(93) is the embellishment placement
(94) is the plastic casing of the gel bubble
(95) is the gel material FIG. 3 is the oblong shaped aromatherapy body cooler. It is formed into a pouch by cutting the fabric on the fold at the bottom and stitched up the sides, turned inside out and lightly pressed. Through the top opening a funnel is used to fill it ¾ full with the herbal stuffing and then pinned tightly to allow straight stitch closure and over lock finishing on the right side up on the top back side of the pouch to indicate proper professional finishing with matching thread. The marabou feather trim is cut in 3" lengths from a long boa. Each end piece is trimmed of scratchy parts and secured with clear anti-fray glue to prevent shedding. Each 3" section of marabou is trimmed of fluff on the flat under side down to the spine before gluing the strip to the top margin of the casing.

Once frozen and placed down the front of a bra it delivers astounding and comforting relief from heat and anxiety.

FIG. 3A is the front perspective view of the present invention;
- (2) is one side seam of the fabric casing
- (3) is the marabou feather trim FIG. 3B is the side perspective view of the present invention;
- (1) is the herbal filling
- (2) is the fabric casing
- (3) is the front position of the marabou feathers FIG. 4 is the hand-held gel pad body cooler. It is cut from a single piece of fabric on the bottom fold. It is stitched with right sides together with webbing strap material placed across the inside center to attach into both side seams. Once trimmed, turned right side out and pressed, a flat self-contained gel pack is inserted in through the top opening. The top fabric lips are turned tightly into the casing and top stitched closed.

FIG. 4A is the plan under side of said invention;
- (32) is the fabric casing
- (33) are the brush tines FIG. 4B is the longitudinal cross section of the present invention;
- (31) is the gel material
- (32) is the outer fabric casing
- (33) is the brush tines
- (34) is the strap webbing FIG. 5 is the gel neck wrap body cooler. A chain is created with three self-contained gel packs connected together at each end with elastic with a piece of insulator material laid on top of each gel pack independently on the plan top side. Each end of each piece of insulator is secured by stitching the ends right on top of the end tabs of each gel pack and stitched over the same stitching that connects the gel packs with elastic.

FIG. 5A is a fabric casing made from a length of fabric cut on the bias. Two loop pads are stitched strategically in place an inch apart close to one end of the length of fabric before the fabric is folded lengthwise with right sides together, stitched and trimmed close to the stitching and turned inside out and pressed flat forming a casing. The strip of connected gel packs are then threaded into the fabric casing and centered, leaving 3 or more inches of raw material on either end to create the strap and hook and loop closure. Each section is separated with top traverse stitching through all layers.

FIG. 5A is the plan view of the present invention
- (19) is the top traverse stitching to separate each section
- (23) is the outer fabric casing
- (24) is the stitching around the perimeter of each piece of hook and loop
- (25) is the loop pad
- (26) is the hook pad
- (27) is the strap loop
- (28) is the strap end
- (29) is the tongue FIG. 5B is the lateral cross section of the present invention;
- (16) is the plastic wrapper containing the gel material
- (18) is the connection point of the plastic wrapper end tab, the elastic and the insulator.
- (19) is the top traverse stitching separating each section
- (20) is the insulator The tongue is created by cutting the raw end of the casing to a point and folding the two sides slightly in and over twice and top stitching through all layers to secure. Then the #26 hook pad is stitched into place through all layers on the right side of the fabric casing at the tongue.

The strap is created by cutting the other end of the casing slightly on an angle to a point at the end and folding it in and down twice over an inserted 3 inch strip of thin bias tape in the form of a loop and top stitching through all the layers to secure.

FIG. 5D is the longitudinal cross section of the inner and outer layers of the present invention;
- (16) is the plastic wrapper containing the gel
- (17) is the side stitching of the fabric casing
- (20) is the insulator
- (22) is the gel material
- (23) is the outer fabric casing FIG. 5C is the exploded view of the adjustment process;
- (23) is the outer fabric casing
- (25) is the loop pad
- (26) is the hook pad
- (27) is the strap loop
- (28) is the strap end
- (29) is the direction of the tongue as threaded through the strap loop to attach the hook pad to the loop pad.

Once frozen and laid around neck or head the gel neck wrap delivers an astounding sense of well-being while relieving the stress of body heat and anxiety for a period of time.

What is claimed is:

1. A hand-held body cooling device comprising:
   a closed fabric encasement prepared from a single piece of fabric and having opposing spaced apart front and back walls joined at their periphery, opposing first and second side seams forming a portion of the periphery;
   a strap comprising a flat webbing having first and second opposing sides and crossing the mid-portion of the back wall, the first end of the flat webbing secured in the first side seam and the second end of the flat webbing secured in the second side seam;
   a gel pack comprising a sealed plastic wrapper encasement having generally the shape of the closed fabric encasement, the plastic wrapper encasement filled with gel material, the gel pack enclosed within the enclosed fabric encasement pocket; and
   a brush element comprising a generally planar backbone with a plurality of brush tines extending upward perpendicularly from the backbone, the backbone secured to the front side of the fabric casing.

2. The cooling device according to claim 1 wherein the brush is positioned perpendicular with respect to the strap.

3. The cooling device according to claim 1 wherein the brush is positioned on a portion of the periphery of the enclosed fabric encasement pocket.

4. The cooling device according to claim 1 wherein the brush element is secured in a mid-portion of the front wall of the enclosed fabric encasement pocket.

* * * * *